(12) United States Patent
Johnson

(10) Patent No.: US 6,414,754 B1
(45) Date of Patent: Jul. 2, 2002

(54) METHOD AND APPARATUS FOR SUPPRESSING STRAY LIGHT IN PARTICLE DETECTORS

(75) Inventor: Joel C. Johnson, Lake Oswego, OR (US)

(73) Assignee: Pacific Scientific Instruments Company, Grants Pass, OR (US)

( * ) Notice: Subject to any disclaimer, the term of this patent is extended or adjusted under 35 U.S.C. 154(b) by 0 days.

(21) Appl. No.: 09/521,233

(22) Filed: Mar. 8, 2000

(51) Int. Cl.⁷ ............................................. G01N 21/00
(52) U.S. Cl. .................... 356/338; 356/339; 250/222.2; 372/22
(58) Field of Search ................................ 356/336, 337, 356/338, 339, 340, 341, 342, 343; 250/574, 575, 423 R, 222.2; 372/22, 51, 53

(56) References Cited

U.S. PATENT DOCUMENTS

| | | | | |
|---|---|---|---|---|
| 3,985,453 A | * | 10/1976 | Nakano et al. | 250/574 |
| 4,162,404 A | * | 7/1979 | Fite et al. | 250/423 R |
| 5,459,569 A | * | 10/1995 | Knollenberg et al. | 356/338 |
| 5,642,193 A | | 6/1997 | Girvin et al. | 356/339 |
| 5,946,092 A | | 8/1999 | DeFreez et al. | 356/336 |
| 5,946,093 A | | 8/1999 | DeFreez et al. | 356/339 |
| 6,011,622 A | * | 1/2000 | Fishkin et al. | 356/339 |
| 6,016,194 A | | 1/2000 | Girvin et al. | 356/337 |
| 6,091,494 A | * | 7/2000 | Kreikebaum | 356/336 |

OTHER PUBLICATIONS

"Surface Scattering," vol. 1, chapter 7 "Handbook of Optics," second edition, McGraw Hill (1995), ISBN 0–07–047740–X.
"Defect Scattering," vol. 1, chapter 7, p. 7.6 (Included in chapter 7 ibid.) "Handbook of Optics," second edition, McGraw Hill (1995), ISBN 0–07–047740–X.
"Control of Stray Light," vol. 1, chapter 38 "Handbook of Optics," second edition, McGraw Hill (1995), ISBN 0–07–047740–X.
"Contamination Levels," vol. 1, chapter 38, p. 38.18 (Included in chapter 38 ibid.) "Handbook of Optics," second edition, McGraw Hill (1995), ISBN 0–07–047740–X.
"Thin–Film Manufacturing Considerations," vol. 1, chapter 42, p. 42.14 "Handbook of Optics," second edition, McGraw Hill (1995), ISBN 0–07–047740–X.
"Surface and Interface Imperfections," vol. 1, chapter 42, p. 42.44. "Handbook of Optics," second edition, McGraw Hill (1995), ISBN 0–07–047740–X.
"Molecular Rayleigh Scattering," vol. 1, chapter 44, p. 44.14 "Handbook of Optics," second edition, McGraw Hill (1995), ISBN 0–07–047740–X.
"Scatter," vol. 2, chapter 33, p. 33.29 "Handbook of Optics," second edition, McGraw Hill (1995), ISBN 0–07–047740–X.
Sandcolor Process Manual, 6 pages (1986?).
Schäfer, F.B. et al., "Dye Lasers," pp. 6–9, Springer–Verlag (1973).
SAF, Batch and Coil Anodizing, 2 pages, (http://www.saf.com/bachncd.html), (Jan. 1994?), printed Feb. 2, 2000.
"Current Anodizing Process," 15 pages, (http://anodizing.org/html/processes.html), (1998), Feb. 2, 2000.

* cited by examiner

Primary Examiner—Frank G. Font
Assistant Examiner—Sang H. Nguyen
(74) Attorney, Agent, or Firm—Stoel Rives LLP

(57) ABSTRACT

A preferred OPTICAL BLACK™ ionic anodize process of the present invention applies a porous anodic oxide coating to a component part in a standard sulfuric acid anodizing bath (with or without organic additives). A modified alternating electric current is then applied to the porous oxide coating to remove excess anodizing electrolyte and to allow the coloring solution access to the pores. The oxide coating is electrolytically colored in a low pH acid bath containing a tin salt, sulfuric acid, and organic additives. Alternating current carries additional tin salt to the base of the pores where the tin salt is reduced to metallic tin or tin oxide. Others metals or metallic salts could be employed. Component parts treated by the OPTICAL BLACK™ ionic anodize process can be advantageously employed in optical systems, such as particle detectors, to reduce or eliminate stray light.

39 Claims, 3 Drawing Sheets

METHOD AND APPARATUS FOR SUPPRESSING STRAY LIGHT IN PARTICLE DETECTORS

TECHNICAL FIELD

This invention relates to particle detection systems and, in particular, to a method and apparatus to suppress generation or propagation of stray infrared light within particle counting systems.

BACKGROUND OF THE INVENTION

Conventional particle counters measure scattered light from particles traversing a sample area illuminated by a light source. In scattered light sensing systems, any background source light that is scattered by internal cavities of the particle counter that is not associated with light scattered by particles will decrease the ratio between the scattered light signal and the background light signal. If the internal cavities of the particle detector are highly reflective, the light reflected off the walls due to any off-axis re-circulating particles can also be reflected back into the particle detector and detected as particles. Light blocking particle detection systems measure the reduction of light intensity blocked by particles traversing the viewing area. In light blocking systems, light that is scattered from the particles and reflected back into the detector will decrease the ratio between a particle detection signal and background noise. The same is true for any light that is reflected around the sample area and not used to sample particles. Undesirable detection of such stray radiation can create particle detection signals that can mislead the particle detection analysis of such signals.

Conventional particle counters employ visible wavelength lasers for a light source and are often fabricated from aluminum that is then black anodized to suppress unwanted internal reflection. Common black anodizing entails creating a porous layer of aluminum oxide on the surface of an aluminum part, such as an internal wall of a particle counting system. The part is subsequently soaked in an organic dye to create the black "color," and then the dye is sealed into the part. The color black is actually a mixture of a number of different dyes, each of which absorbs a portion of the visible spectrum.

New generations of particle detectors are using different light sources including diode lasers that emit light in the near infrared wavelength region. Particle detectors employing different wavelengths have been more prone to experience stray light problems.

SUMMARY OF THE INVENTION

An object of the present invention is, therefore, to provide a particle system or method that employs light including a nonvisible wavelength, such as IR or UV, and suppresses stray light.

Another object of the invention is to provide such a system or method that employs an ionic anodize process to treat appropriate system components exposed to light.

Applicant's graduate school work with organic dye lasers led him to recall that it was very difficult, if not impossible, to create chemically stable organic dyes that would absorb or lase near infrared light. He thus suspected that stray light problems associated with new generation particle detectors might be caused by the dyes used in the anodize process because such dyes might not be sufficiently effective in the infrared spectrum. He also speculated that organic dyes that might be initially effective in the infrared and used in the anodize process might also be chemically unstable in infrared applications.

The appropriate components of particle detectors of the present invention are anodized with an ionic coloring agent, instead of a traditional organic coloring compound, deposited into the porous aluminum oxide. Such appropriate components include, but are not limited to, optically or electrically nonfunctional internal components whose surfaces are off-axis from the light generation and detection axes. Because the atoms of ionic agents are more tightly bound and are not characterized by many of the energy transfer mechanisms available to the conventional organic anodize dyes, an ionic coloring process provides anodized parts that are more spectrally uniform.

A preferred OPTICAL BLACK™ ionic anodize process of the present invention applies a porous anodic oxide coating in a standard sulfuric acid anodizing bath (with or without organic additives), subjects the porous oxide coating to a modified alternating electric current to remove excess anodizing electrolyte and to allow the coloring solution access to the pores, and electrolytically colors the oxide coating in a low pH acid bath containing a tin salt, sulfuric acid, and organic additives. Alternating current carries additional tin salt to the base of the pores where the tin salt is reduced to metallic tin or tin oxide. Others metals or metallic salts could be employed.

Additional objects and advantages of this invention will be apparent from the following detailed description of preferred embodiments thereof which proceeds with reference to the accompanying drawings.

DETAILED DESCRIPTION OF THE PREFERRED EMBODIMENTS

Figure 1:
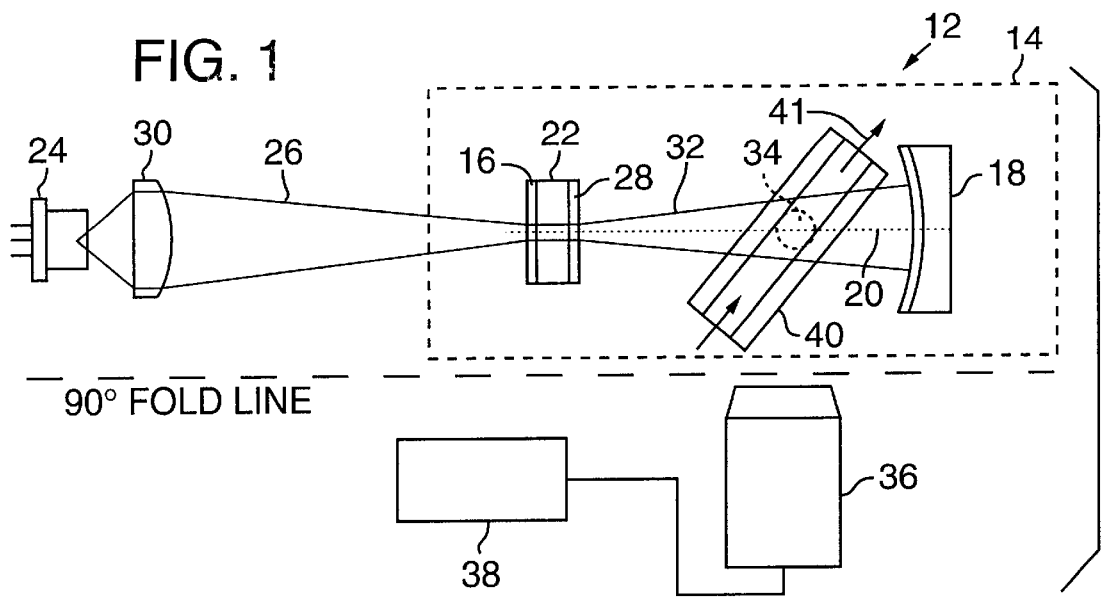
FIG. 1 is a simplified plan view of a generic particle detection system for detecting particles in a gas or a liquid.

FIG. 1 shows a simplified plan view of composite generic embodiment of a particle detection system 12, such as a particle counting system, for detecting particles in a gas or a liquid stream having component parts treated by an OPTICAL BLACK™ ionic anodize process in accordance with the present invention. With reference to FIG. 1, a preferred particle detection system 12 includes a resonator cavity 14 defined by two spaced-apart mirrors 16 and 18 positioned along an optical axis 20. A laser medium 22 is also positioned within resonator cavity 14 along optical axis 20 and between mirrors 16 and 18, which may be dielectric mirrors and are highly reflective to the wavelength of emission radiation 32 generated by laser medium 22. Furthermore, mirror 16 may be formed on or into the surface of laser medium 22 and is highly transmissive to the wavelength(s) of pumping radiation 26. Surface 28 of laser medium 22 preferably has an antireflection coating.

A pumping source 24 generates the pumping radiation 26, which is optically coupled through beam-shaping optics 30, into laser medium 22 to produce a beam of emission radiation 32 that propagates along optical axis 20. Emission radiation 32 could be Q-switched, but is preferably generated in continuous wave (cw) to avoid missing particles that could flow through a view volume 34 during an interpulse period that would be created by the Q-switch. View volume 34 is positioned along optical axis 20 between mirror 18 and laser medium 22 and is generally defined by an intersection between a flow path 41 and emission radiation 32. A fluid containing target particles is introduced into view volume 34 so that the emission radiation 32 can impinge upon the target particles and cause them to scatter light.

When the fluid comprises a liquid, such as deionized water, detection system 12 employs a sample or flow cell 40 to contain a liquid sample or a liquid stream. Flow cell 40 may optionally be employed when the fluid stream comprises a gas, particularly if the gas is not air.

A radiation-sensitive detector 36 is disposed to sense light scattered from view volume 34 and produce signals, a property of which is proportional to the light that it senses. Typically, detector 36 is positioned to sense light scattered in a direction transverse to both optic axis 20 and a direction of fluid flow, and preferably perpendicular to them. A processing device 38, such as a pulse height analyzer, is in electrical communication to receive signals produced by detector 36 to quantitatively analyze the intensity of the light sensed to determine the number and size of particles in accordance with conventional analytical methods.

Undesirable detection of stray radiation by detector 36 can create particle detection signals that can mislead the quantitative analysis of such signals. Stray radiation in conventional particle detecting systems has a number of sources. Below is a brief description of certain sources that can create significant noise that can be suppressed by employing OPTICAL BLACK™ ionically anodized part in accordance with the present invention. All references included below, and not otherwise identified, are from "Handbook of Optics," second edition, volumes 1 and 2, McGraw Hill (1995), ISBN 0-07-047740-X.

One source of stray radiation includes laser pumping radiation 26 that is not absorbed by lasing medium 22. Another source of stray radiation includes spontaneous emission radiation 32 of laser medium 22 that does not propagate in the beam direction and emits in all directions. Spontaneous emission comes from a laser medium when pumped with a wavelength in it absorption region. Stray radiation may also include spontaneous emission radiation 32 of wavelengths that are not in the beam propagation wavelength because they are below lasing threshold and/or are outside the reflectance of the laser mirrors.

Another source of stray radiation includes scatter from optical interfaces. This type of scattering is different from the scattered radiation emitted by target particles and is generally described in "Surface Scattering," volume 1, chapter 7. One type of surface scattering includes defect scattering where imperfections in the polish on the optical interfaces or surfaces of optics that the laser beam passes through scatter light. Small micro scratches, pits or bumps, on the size order of microns cause a small portion of the laser beam light to scatter. This type of scattering is described in detail in "Defect Scattering," volume 1, chapter 7, page 7.6.

Another type of surface scattering includes contamination scattering where particles on the surfaces of the optics scatter light from the beam in much the same way that defects scatter light. This type of surface scattering is described in detail in "Contamination Levels," volume 1, chapter 38, page 38.18. Imperfections in the coatings, which include surface irregularities and inclusions, of optical and nonoptical components, can also be a source of surface scattering. This type of surface scattering is described in detail in "Thin-Film Manufacturing Considerations," volume 1, chapter 42, page 42.14 and "Surface and Interface Imperfections," volume 1, chapter 42, page 42.44.

Another source of stray radiation includes internal scatter from imperfections in the material, inclusions, and bubbles in the optical materials. This type of scattering is described in detail in "Scatter," volume 2, chapter 33, page 33.29.

Diffraction from light stops or baffles that are put around the laser beam to reduce the amount of scattered light entering into view volume 34 where target particles are detected can also be the source of stray radiation. This type of stray radiation is described in detail in "Control of Stray Light," volume 1, chapter 38. In a preferred embodiment, the laser beam emitted from solid-state laser medium 22 in particle detection system 12 has a single transverse mode, TEM 0-0, gaussian intensity profile. Gaussian beams have a small amount of power extending 3 to 4 times the $1/e^2$ diameter of the beam. Baffle sizes are therefore preferably small enough to keep out stray light but not so small that they interfere with the beam. Nevertheless, a small amount of the beam typically does contact the baffle edge and diffracts around it.

Another source of stray radiation includes radiation scattered by the molecules of the fluid passing through view volume 34 and carrying the target particles. This type of stray radiation is described in detail in "Molecular Rayleigh Scattering," volume 1, chapter 44, page 44.14.

A conventional light trap 54 (FIG. 2) that is used to trap the laser beam that passes through a view volume (and that is not an intracavity laser, or light extinction sensor) is not a perfect light absorber. Thus, stray radiation can also include a small amount of radiation that reflects back into the area of view volume 34 out of light trap 54.

Skilled persons will appreciate that many variations in particle counter design are possible and contemplated for implementation of the invention. For example, OPTICAL BLACK™ ionically anodized parts can be employed in particle counting systems, such as those described in U.S. Pat. No. 5,642,193 of Girvin et al., with multiple cavities or different positions of the view volumes with respect to the cavities or other optical components. OPTICAL BLACK™ ionically anodized parts can also be employed in dual laser heterodyne systems, such as those described in U.S. Pat. No. 5,946,092 of DeFreez et al. and U.S. Pat. No. 6,106,194 of Girvin et al. These sensing systems typically employ visible, near IR, or IR radiation, utilizing preferred wavelengths or wavelength ranges, including but not limited to, 532 nm, 633 nm, 780 nm–830 nm, and 1064 nm as well as other wavelengths disclosed in these patents. In addition, OPTICAL BLACK™ ionically anodized parts are especially useful in particle counting systems that employ an upconversion laser and utilize both UV and IR radiation, such as the particle counting systems disclosed in U.S. Pat. No. 5,946,093 of DeFreez et al. OPTICAL BLACK™ ionically anodized parts are also especially useful in biological particle detection or counting systems that employ UV excitation and/or IR fluorescence detection of particles, such as the systems disclosed in U.S. patent application Ser. No. 09/191,493, filed on Nov. 13, 1998, of DeFreez et al. Preferred UV wavelengths include, but are not limited to, 266 nm and 355 nm as well as other wavelengths disclosed in these patents.

Table I below lists a variety of MET ONE™, HIAC™, or ROYCO™ products and sensors that preferably employ component parts treated with the OPTICAL BLACK™ ionic anodizing process:

TABLE I

| Sensor No. | System Description |
| --- | --- |
| 2981190 | 1010-Light Blocking, 1 μm Sensor Assembly |
| 2081210 | 1010-Light Blocking, 1 μm Sensor with Nema Rated Enclosure |
| 2080995 | 1020-Light Blocking Sensor Assembly |
| 2081039 | 1020-Light Blocking, 2 μm Sensor with Nema Rated Enclosure |
| 203773 | 211 Sensor |
| 204793 | 211 0.3 μm Sensor with Nema Rated Enclosure |
| 204880 | 4 Port Sensor |
| 2080294 | 70° Sensor, Solid State |
| 2080316 | 70° Sensor, 0.1 Cubic Foot Per Minute |
| 2080453 | 70° Sensor, 0.01 Cubic Foot Per Minute |
| 2080455 | 70° Sensor, 0.3 μm |
| 2080909 | 1100/1104 Sensor, Condensation Nucleus Counter |
| 2083999 | Micro Sensor 0.3/0.5 μm |
| 2081424 | Dedicated Water Sensor |
| 2081470 | Teeny HeNe Sensor |
| 2082096 | Dual Port Sensor |
| 2082640 | 3 Port Sensor |
| 2082956 | 1107 CNC Sensor |
| 2083136 | 0.1 Teeny HeNe Sensor, Condensation Nucleus Counter |
| 2083235 | 70°, 0.3 μm Sensor, 1 Cubic Foot Per Minute |
| 2083546 | Dedicated Water Sensor |
| 2084086 | 70°, 0.3 μm Sensor, 1 Cubic Foot Per Minute MC100/200 PALL PORT, PORT PLUS 5230,5250 HRLD CE HR/LD SENSORS MC-05/SEL PCS/OLVS/B60/160 |

Figure 2:
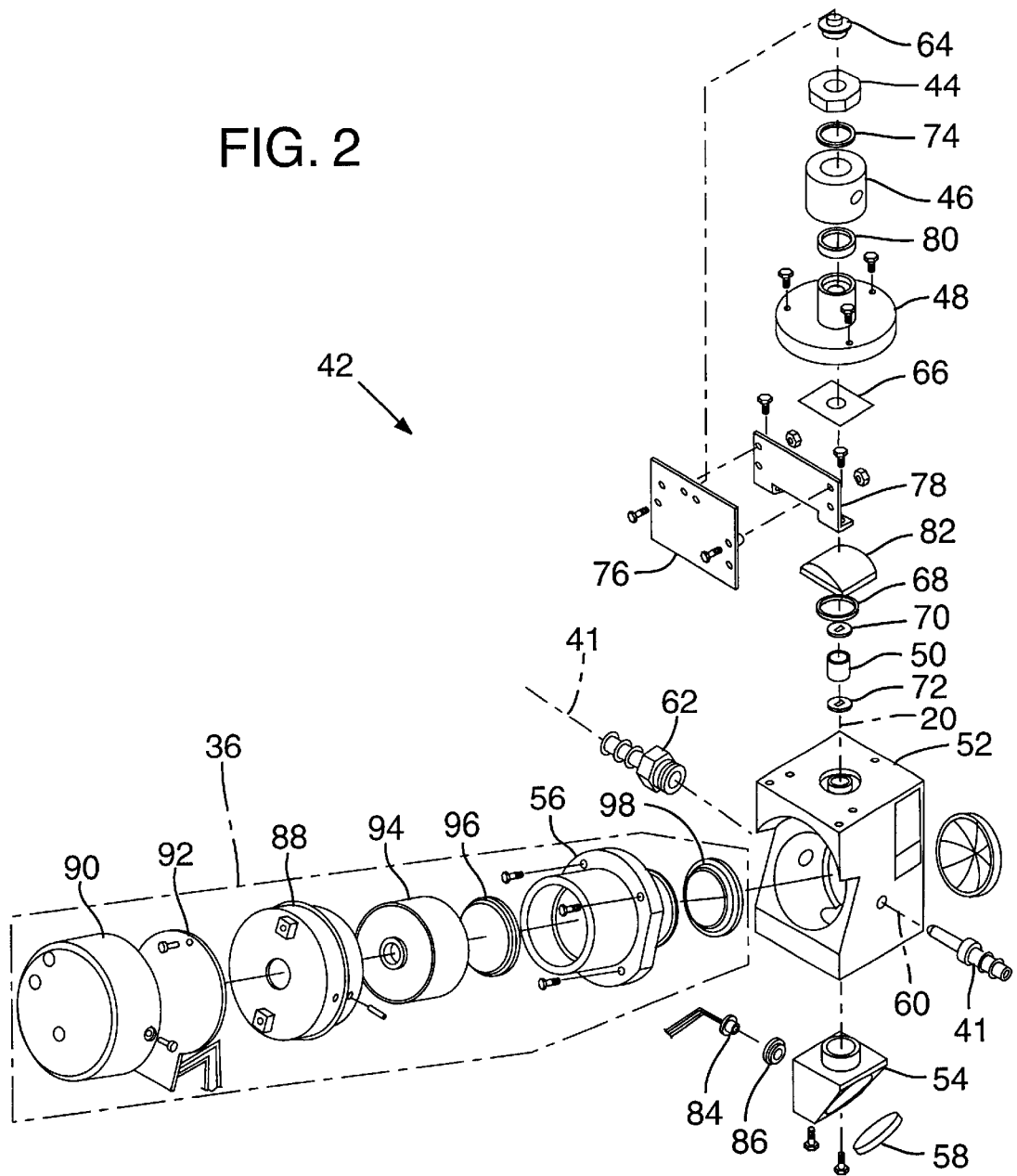
FIG. 2 is an exploded view of a generic particle detection system showing various component parts.

FIG. 2 shows various component parts and their arrangement in another exemplary particle detection system 42. The component parts of particle detection system 42, or other detection systems, that are preferably treated with the OPTICAL BLACK™ ionic anodize process to be optically absorbing include an emitter carrier 44, such as part number 204623 or analogous part numbers 2083553, 2084089, 2080124, or 2080124-01 from other sensing systems; an emitter slide 46, such as part number 204618 or analogous part numbers 2083555, 2080126, 2084090, or 2081675 from other sensing systems; a cylindrical or other lens mount 48, such as part number 204405-2 or analogous part numbers 2084091, 2080778, 2080893 from other sensing systems; light baffle spacer 50, such as part number 2083231; system or sensor housing or body 52, such as part number 2083237 (70°) or analogous part numbers 2080417 (70°), 2082095 (dual port), 204820 (three port), 2083548 (dedicated water), 2081639 (dedicated water sensor), 2081469 (block), 2080917 (micro), 2080885, 2080267, or 2080267-1 from other sensing systems; light trap 54, such as part number 2083233 or analogous part numbers 204863, 204892, 204939-1, 204939-2, 204939-3, 2081465, or 2081472 from other sensing systems; and a collection or other lens holder or mount 56, such as: part number 2080430 or analogous part numbers 2080868, 2080863-1, 2080430, 2080788, 2083796, 2083885, 2080414, 203543, 203543-1 from other sensing systems.

Skilled persons will appreciate that treating housings 52 and light traps 54 by the OPTICAL BLACK™ ionic anodize process provides significant reduction in stray light, and treating the other component parts of particle detection systems 12 and 42 provides incremental benefit. Skilled persons will also appreciate that light absorbing glass 58 of light trap 54 can be replaced with OPTICAL BLACK™ aluminum. The exposed surfaces of component parts of flow path 41, such as nozzle 60 and exit 62, can also be treated to be optically absorbing.

The part,numbers and descriptions of other system components, from a variety of particle detection system products, that are preferably treated by the OPTICAL BLACK™ ionic anodize process in accordance with the present invention include: 2081033 light baffle; 2080763-1 collimator lens mount; 2081431 collimator lens mount; 2083552 collimator lens mount; 204937 nozzle inlet plate; 2081637 detector mount; 2081528 inlet plate; 2081468 clean out cover; 2081185 optics holder; 203523-1 objective lens slide; 203524 housing slide; 2080183 objective lens sleeve; 204568-1, -2, -3 isolator window; 2080867 optics-holder; 2081184 optics holder spacer; 203544, -1 lens housing; 2081637 detector mount; 2080294 photo diode mount; 2083549 cell lens retainer; 203535 laser diode mount; 2082866 laser mount; 2081609 laser mount; 2083883-1 external mirror holder; 2081466 mirror mount plate; 2083156-01 mirror mount plate; 2084176 mounting plate; 070168-03, 05 type 2 lens mount; 070166-03 collimating lens mount; 070112-03 I.d. lens system holder; 070113-03 collimator holder; 091148-03 laser diode barrel; 091154-03 negative lens holder; 071117-03 weight relev'd sensor body; 068112-03 mdl 2230/5230 sensor body; 6114-03 lens holder; 070182-03, -05 sensor body; 04210603 electronics holder; 040c100-03 sensor body; 040115-03 laser diode holder; 040114-03 laser diode front housing; 040118-03 lens holder; 0408102-03 negative lens holder; 047142-03 filter holder; 047149-03 lens holder; 046134-03 receiver optics housing; 047147-03 front housing; 047132-03 laser diode holder; 047130-03 hps lens holder; and 047154-03 photo diode holder.

With reference again to FIG. 2, a skilled person can also optionally treat exposed surfaces of other component parts, if made from aluminum, surrounding optical axis 20, propagating from diode laser 64 in optical detection system 42, for less significant benefit. Such component parts include: spacer 66, O-ring 68, and apertures 70 and 72. Skilled persons will appreciate that certain electrically or optically functional components, such as insulator 74, diode laser driver 76, diode laser driver bracket 78, lens 80, and cylindrical lens 82, are preferably not treated. Similarly, the exposed surfaces of calibration components, such as photo-diode 84 and electrical insulator 86, are preferably not treated.

Although the exposed surfaces of some additional components, such as photoamplifier mount 88, of detector 36 can be treated to be optically absorbing, the exposed surfaces of circuit board cover 90, photoamplifier circuit board 92, electrical insulator 94, lens 96, and lens 98 are preferably not treated. Skilled persons will appreciate that some component parts are preferably made from materials other than aluminum, such as DELRIN™ or carbon-impregnated TEFLON™ or other polymeric or plastic materials that are light absorbing at the desirable wavelengths employed by the sensing system.

Figure 3:
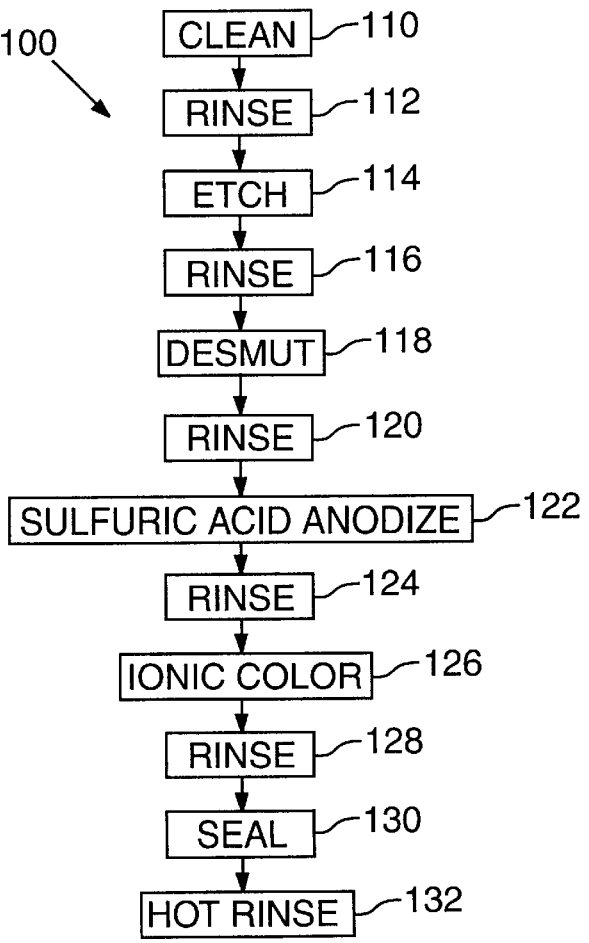
FIG. 3 is flow diagram of a preferred ionic anodize process for treating system components in accordance with the present invention.

FIG. 3 is flow diagram of a preferred OPTICAL BLACK™ ionic anodize process 100 for treating system components in accordance with the present invention. The preferred OPTICAL BLACK™ and similarly suitable ionic anodize processes can be performed by +1Anodize of Sherwood, Oreg.

With reference to FIG. 3, the process steps are preferably performed in the different containers, but some steps can be performed in the same containers. Preferred racking or transporting methods employ metal racks constructed of titanium or aluminum and are chemically stripped between loads. These racks can be plastic coated. Clamps or contacts are preferably more numerous and larger and heavier than those used for decorative anodizing applications.

System components to be subjected to the OPTICAL BLACK™ ionic anodize process 100 are preferably cleaned in a cleaning step 110 with a heated, non-silicated, non-chelated, non-phosphated, non-etching cleaner, such as a sodium tetraborate based cleaner. However, mildly etching and phosphated cleaners can also be employed. The cleaning time will depend on the type and nature of the soils to be removed. If the system components have been buffed, a subsequent cleaner that is acidic and non-etching may be used. Clean, oil-free air agitation around the cleaning container or chamber is preferred. Skilled persons will appreciate that a variety of other cleaning agents could be employed.

Cleaning step 110 is preferably followed by a rinsing step 112 that entails two counter-flow rinses with clean water.

A preferred etching step 114 employs about 5–10% NaOH (and additives to improve speed and/or uniformity). Etching step 114 is preferably performed in a steel or plastic tank at a temperature of about 55–60° C. (131–140° F.) under clean, oilfree air agitation for one to ten minutes, preferably 1–2 minutes, to remove about 0.3–0.8 mil (7–20 microns), preferably 0.3–0.5 mil, of metal from the system component. Skilled persons will appreciate that a variety of other etch concentrations and agents could be employed.

Etching step 114 is preferably followed by a rinsing step 116 that entails two counter-flow rinses with clean water.

A preferred desmutting step 118 employs about a 7–10% sulfuric acid and 3–5% Novox 320 (Henkle Products) solution, or a 15–30% solution of nitric acid. Desmutting step 118 is preferably performed in a stainless steel or PVC tank at about room temperature 20–22° C. (68–72° F.) with clean, oil-free air agitation for one to ten minutes, preferably five to ten minutes, depending on the amount of smut to be removed from the system component. Skilled persons will appreciate that a variety of other desmutting concentrations and agents could be employed.

Desmutting step 118 is preferably followed by a rinsing step 120 that entails two counter-flow rinses with clean water.

A preferred acid anodizing step 122 employs about 165–185 g/l of "free" sulfuric acid and 4–18 g/l aluminum, more preferably 12–18 g/l aluminum. Acid anodizing step 122 is preferably performed in a PVC-, polypropylene-, or KOROSEAL™-lined, fiber glass tank at about room temperature 20–22° C. (68–72° F.) with clean, oil-free air agitation for 50 minutes and 1.4 amp/sq dm (15 ASF) to apply a film thickness of at least 20 microns (0.8 mil) to the system component. Preferably, the liquid level in the anodizing tank is higher than that of the ionic coloring tank. Preferably the voltage is ramped up over a period of 0.5–1 minute and ramped down over 30 seconds at the end of the DC cycle. Skilled persons will appreciate that a variety of other acid anodizing concentrations and agents could be employed.

Acid anodizing step 122 is preferably followed by a rinsing step 124 that entails two counter-flow rinses with clean water.

A preferred OPTICAL BLACK™ ionic coloring step 126 employs about 9–11 g/l of stannous tin, 18–20 g/l of stabilizer, and 20 g/l of sulfuric acid. OPTICAL BLACK™ ionic coloring step 126 is preferably performed in a tank lined with an acid-resistant, non-conductive material at about room temperature 20–22° C. (68–72° F.) under clean, oil-free air agitation for ten minutes to three hours, preferably about 13 minutes, at 15 to 25 volts DC, preferably about 19 volts. No bare (unanodized) aluminum should be introduced to the tank.

Two counter lectrodes are mounted on the sides of the tank with the bus bars at least about 300 mm–1000 mm (or about 1' to 3') apart. The counterelectrodes are preferably long enough to be slightly more deeply submerged in the bath than the system component is submerged and are of stainless steel, e.g., 316 grade or austenitic. They may be constructed in any desired form, such as strips or sheets, corrugated or angular, or of tubular or of circular shape.

In a preferred embodiment, the OPTICAL BLACK™ coloring bath employs either the SANDOCOLOR® Salt T liquid (or SANDOCOLOR® TS-2 Liquid), which contains the preferred proportions of tin and SANDOCOLOR® Stabilizer, or powdered tin sulfate plus additional SANDO-COLOR® Stabilizer.

A chloride-free tin sulfate ($SnSO_4$) is preferably employed. The tin sulfate incurs about a 3–5% loss of $SnSO_4$ upon make-up and gradually diminishes due to real consumption as well as drag-out and oxidation to tetravalent tin. The sulfuric acid provides conductivity suitable for the coloring step 126 and helps prevent hydrolysis of the tin sulfate. The stabilizer improves the metal stability of the electrolyte and contributes to uniform coloring.

The coloring bath is created by partly filling the tank with distilled and/or deionized water and then adding in consecutive order 1 gallon of concentrated sulfuric acid ($H_2SO_4$ and 10 gallons of SANDOCOLOR® Salt T Liquid, for each 100 gallons of final bath. The tank is then filled to its final volume, and the coloring solution is mixed, analyzed, and adjusted to the final desirable concentrations.

If the coloring bath is instead to be created with powdered tin sulfate, 1 gallon of concentrated sulfuric acid ($H_2SO_4$), 2 gallons of SANDOCOLOR® Stabilizer Liquid, and about 16.7 pounds of tin sulfate ($SnSO_4$) are added to the tank. SANDOCOLOR® TS-2 Liquid, on the other hand, is merely diluted with the water at a ratio of 10:1 and the sulfuric acid concentration adjusted to 18 g/l.

The system components are slowly immersed at a slanted angle in the coloring bath to minimize trapping air bubbles against the components. The components can be agitated up and down multiple times in the bath to reduce the amount of trapped air bubbles, or mechanical agitation may be used by circulating the solution with a pump.

The coloring bath tends to cloud due to precipitation of relatively insoluble compounds of tetravalent tin. This precipitated material is preferably removed by filtering. A preferred filtration system employs acidic-suitable filter cartridges of 15–20 micron size and completely circulates the coloring solution every 2–3 hours.

The coloring bath concentrations are monitored to promote uniform coloring. Under operating conditions, the stabilizer is preferably added in 1:1 proportion to the addition of tin sulfate, or SANDOCOLOR® TS-2 Liquid is added to maintain a concentration of 18 g/l. The stabilizer should also be replenished.

OPTICAL BLACK™ ionic coloring step 126 is preferably followed by a rinsing step 128 that entails two counter-flow rinses with clean water.

A preferred sealing step 130 employs about 5 g/l solution of a sealing salt or a 2–4% nickel acetate solution, such as Anoseal 1000, at a pH of 5.5 to 7.0, preferably about 5.8. Sealing step 130 is preferably performed at a temperature of about 66–88° C. (149–190° F.), preferably 82–88° C. (180–190° F.) under clean, oil-free air agitation for 10 minutes to 30 minutes, preferably about 20 minutes.

An alternative sealing step or optional post sealing step employs about 1–3 g/l of Anodalsh-1 at a pH of 5.5–6.0. Optional sealing step is preferably performed at a temperature of at least 98° C. (208° F.) (boiling).

After component parts are sealed, they are preferably subjected to a hot rinse step 132 that entails rinsing the component parts with water at 66–71° C. (150–160° F.) for about a minute under clean, oil-free air to facilitate drying. The component parts are then dried at room temperature or in a warm air dryer.

Figure 4:
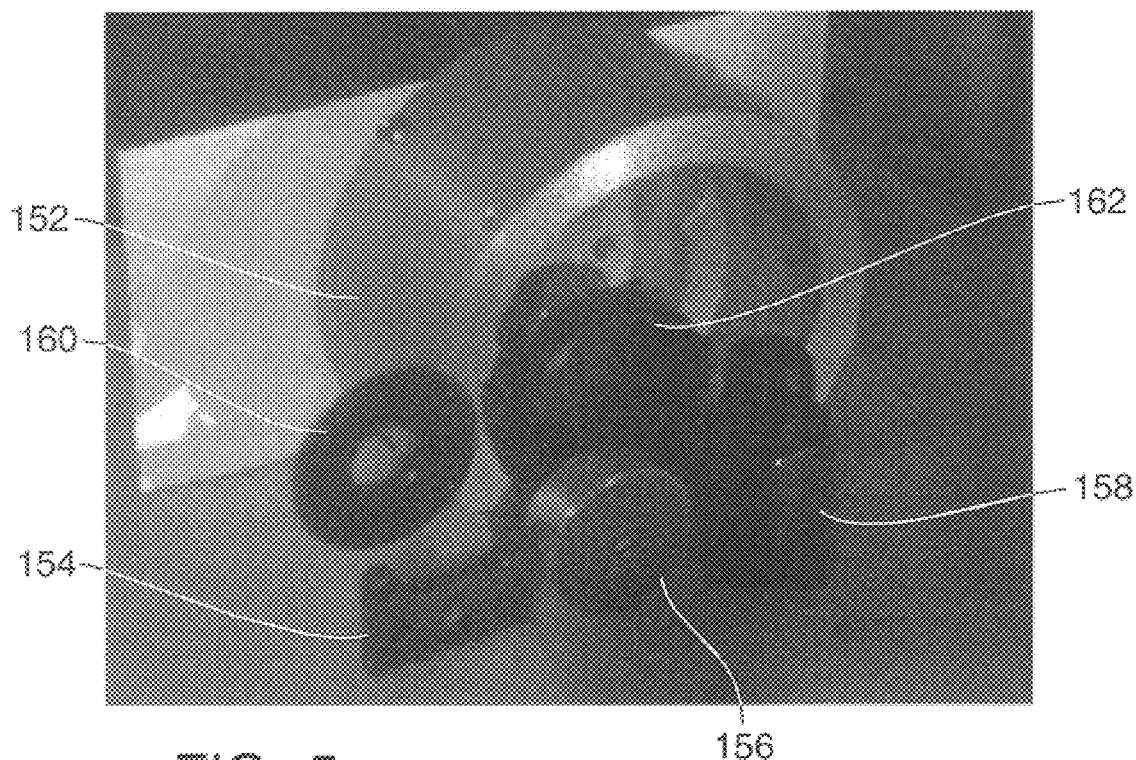
FIG. 4 is a copy of an electronic photograph showing the amount of light reflected off an assortment of sensing system parts, having different light absorbing treatments, under 809 nm laser light.
Figure 5:
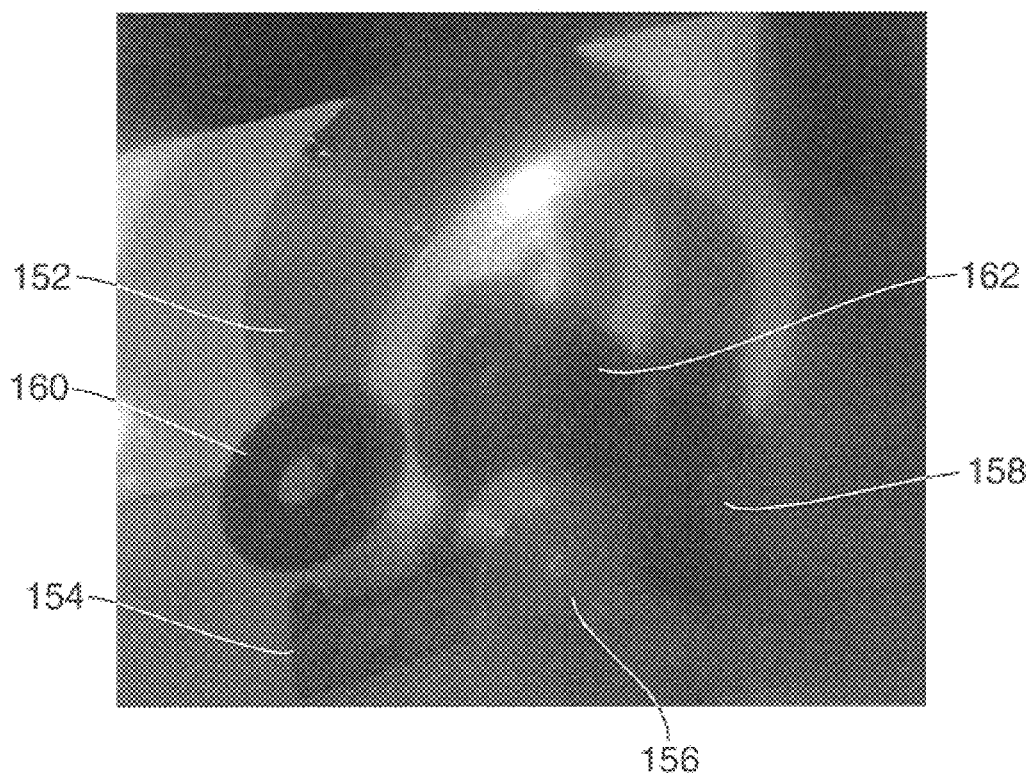
FIG. 5 is a copy of an electronic photograph showing the amount of light reflected off an assortment of sensing system parts, having different light absorbing treatments, under 1064 nm laser light.

FIGS. 4 and 5 are copies of electronic photographs showing the amount of light reflected off an assortment of sensing system parts, having different light absorbing treatments, under low level background incandescent light and respective 809 nm laser light and 1064 nm. With reference to FIGS. 4 and 5, conventionally organically anodized part 152 is highly light reflective to near infrared 809 nm laser light and IR 1064 nm light, but OPTICAL BLACK™ ionically colored part 154 is highly light absorbing to these wavelength. Solar black light trap-painted part 156 is significantly less absorbing than part 154 and is only slightly more absorbing than part 152 at 809 nm, but exhibits even slightly greater reflectivity at 1064 nm. Black oxidized, stainless steel part 158 has good optical absorption properties at these wavelengths, but stainless steel material and machining is about eight to tens times more expensive than aluminum material and machining. Stainless steel oxidation adds a significant thickness to part 158 so the part's original size is not conserved. The OPTICAL BLACK™ ionic anodize process removes material before adding to the surface so the size of part 154 is conserved. The coating resulting from the stainless steel oxidation process is also not as durable as the surface resulting from the ionic anodize process. DELRIN™ part 160 and carbon-impregnated TEFLON™ are not metal but exhibit good light absorption qualities at 809 nm and 1064 nm.

In addition to the above described light absorbing benefits associated with the absorption of stray radiation, sensing systems employing parts treated by the OPTICAL BLACK™ ionic anodize process are more quickly and easily assembled. Particle detection systems employing conventional organically dyed parts require a high degree of exacting alignment and manipulation of optical components to avoid undesirable internal reflection and scattering. Because the stray radiation is largely absorbed, particle detection systems employing OPTICAL BLACK™ treated parts do not require the same degree of such time-consuming adjustments.

Although the present invention is described herein by way of example to particle detection systems that measure scattered light, skilled persons will appreciate that particle detection systems that measure the reduction of light intensity (light blocking systems) will also benefit by employing parts treated by the OPTICAL BLACK™ ionic anodize process.

It will be obvious to those having skill in the art that many changes may be made to the details of the above-described embodiments of this invention without departing from the underlying principles thereof. The scope of the present invention should, therefore, be determined only by the following claims.

What is claimed is:

1. A particle detection system having sources of stray radiation, comprising:
    a light source for generating along an optical path emission radiation having a wavelength;
    a view volume intersecting the optical path, the view volume adapted for receiving a fluid carrying target particles and exposing the target particles to emission radiation propagating along the optical path such that the target particles upon which the emission radiation is incident scatter portions of the emission radiation throughout the particle detection system;
    a radiation-sensitive detector optically associated with the view volume to detect radiation scattered by target particles in the view volume; and
    a component part having one or more surfaces treated by an ionic coloring agent so that stray radiation that impinges upon a treated surface of the component part is absorbed by the treated surface and thereby is undetected by the radiation-sensitive detector.

2. The particle detection system of claim 1 in which the ionic coloring agent comprises an inorganic electrolyte.

3. The particle detection system of claim 2 in which the inorganic electrolyte comprises metal.

4. The particle detection system of claim 3 in which the metal comprises tin.

5. The particle detection system of claim 4 in which the stray radiation comprises an infrared wavelength.

6. The particle detection system of claim 4 in which the stray radiation comprises an ultraviolet wavelength.

7. The particle detection system of claim 1 in which the stray radiation comprises an infrared wavelength.

8. The particle detection system of claim 1 in which the stray radiation comprises an ultraviolet wavelength.

9. The particle detection system of claim 1 in which the surface comprises an internal wall of a particle detection system housing.

10. The particle detection system of claim 1 in which the surface comprises an interior surface of a light trap.

11. The particle detection system of claim 1 in which the particle detection system comprises a particle counting system.

12. The particle detection system of claim 1 in which at least one of the surfaces treated by the ionic coloring agent comprises a metal surface.

13. The particle detection system of claim 12 in which the metal surface comprises aluminum.

14. The particle detection system of claim 1 in which the stray radiation includes at least one of laser pumping radiation, spontaneous emission radiation, emission radiation having a wavelength that differs from the emission radiation wavelength, emission radiation scattered by one of the component parts, and emission radiation scattered by the target particles.

15. A method for detecting particles in a particle detection system having sources of stray radiation, comprising:
    directing along an optical path emission radiation having a wavelength;
    propagating fluid carrying target particles along a flow path through a view volume that intersects the optical path to expose the target particles to emission radiation propagating along the optical path such that the target particles scatter radiation in response to emission radiation that impinges upon the target particles;
    detecting radiation scattered by target particles in the view volume with a radiation-sensitive detector; and employing a component part having one or more surfaces treated by an ionic anodize process so that stray radiation that impinges a treated surface of the component part is absorbed by the treated surface and thereby is undetected by the radiation-sensitive detector.

16. The method of claim 15 in which the ionic coloring agent comprises an inorganic electrolyte.

17. The method of claim 16 in which the inorganic electrolyte comprises metal.

18. The method of claim 17 in which the metal comprises tin.

19. The method of claim 18 in which the stray radiation comprises an infrared wavelength.

20. The method of claim 18 in which the stray radiation comprises an ultraviolet wavelength.

21. The method of claim 15 in which the stray radiation comprises an infrared wavelength.

22. The method of claim 15 in which the stray radiation comprises an ultraviolet wavelength.

23. The method of claim 15 in which the surface comprises an internal wall of a particle detection system housing.

24. The method of claim 15 in which the surface comprises an interior surface of a light trap.

25. The method of claim 15 further comprising:

analyzing detected radiation scattered by target particles in the view volume to determine the number of target particles.

26. The method of claim 15 in which at least one of the surfaces treated by the ionic anodize process comprises a metal surface.

27. The particle detection system of claim 26 in which the metal surface comprises aluminum.

28. The method of claim 15 in which the stray radiation includes at least one of laser pumping radiation, spontaneous emission radiation, radiation having a wavelength that differs from the emission radiation wavelength, emission radiation scattered-by one of the component parts, and emission radiation scattered by the target particles.

29. A method for reducing the effects of stray radiation in a particle detection system, comprising:

anodizing one or more surfaces of an aluminum, interior component part of the particle detection system to make a porous aluminum oxide layer on the surface;

coloring the surface with an ionic coloring agent; and assembling the particle detection system to include the component part so that stray radiation that impinges a treated surface of the component part is absorbed by the treated surface such that the stray radiation is undetected by the radiation-sensitive detector.

30. The method of claim 29 in which the ionic coloring agent comprises an inorganic-electrolyte.

31. The method of claim 30 in which the stray radiation comprises an ultraviolet wavelength.

32. The method of claim 30 in which the inorganic electrolyte comprises metal.

33. The method of claim 32 in which the metal comprises tin.

34. The method of claim 33 further comprising:

introducing at least 9 g/L of chloride-free, tin sulfate into a coloring bath for coloring the component part.

35. The method of claim 33 in which the stray radiation comprises an infrared wavelength.

36. The method of claim 29 in which the surface comprises an internal wall surface of a light trap.

37. The method of claim 29 in which at least one of the surfaces treated by the ionic coloring agent comprises a metal surface.

38. The particle detection system of claim 37 in which the metal surface comprises aluminum.

39. The particle detection system of claim 29 in which the stray radiation includes at least one of laser pumping radiation, spontaneous emission radiation, emission-radiation having a wavelength that differs from the emission radiation wavelength, emission radiation scattered by one of the component parts, and emission radiation scattered by the target particles.

* * * * *